United States Patent
Steinam

(10) Patent No.: US 10,173,615 B2
(45) Date of Patent: Jan. 8, 2019

(54) SYSTEM AND METHOD FOR ADAPTING A VEHICLE COMPONENT USING AN ACTIVE MATERIAL

(71) Applicant: FORD GLOBAL TECHNOLOGIES, LLC, Dearborn, MI (US)

(72) Inventor: Claudia Steinam, Cologne (DE)

(73) Assignee: Ford Global Technologies, LLC, Dearborn, MI (US)

( * ) Notice: Subject to any disclaimer, the term of this patent is extended or adjusted under 35 U.S.C. 154(b) by 85 days.

(21) Appl. No.: 15/378,693

(22) Filed: Dec. 14, 2016

(65) Prior Publication Data
US 2017/0174159 A1    Jun. 22, 2017

(30) Foreign Application Priority Data
Dec. 18, 2015    (DE) .......................... 10 2015 226 041

(51) Int. Cl.
*B60R 16/037* (2006.01)
*B60H 1/00* (2006.01)
(Continued)

(52) U.S. Cl.
CPC .............. *B60R 16/037* (2013.01); *A61B 5/01* (2013.01); *A61B 5/021* (2013.01); *A61B 5/0476* (2013.01); *A61B 5/0816* (2013.01); *A61B 5/165* (2013.01); *A61B 5/18* (2013.01); *A61B 5/681* (2013.01); *B60H 1/00657* (2013.01); *B60H 1/00742* (2013.01); *B60H 1/00821* (2013.01); *B60H 1/00871* (2013.01); *B60H 1/34* (2013.01); *B60H 3/0007* (2013.01); *B60H 3/0014* (2013.01);
(Continued)

(58) Field of Classification Search
CPC ... B60R 16/037; B60R 13/02; B60H 1/00742; B60H 1/00821; B60H 1/3407; B60K 37/04; B33Y 80/00; B32B 2605/003
See application file for complete search history.

(56) References Cited

U.S. PATENT DOCUMENTS

| 6,786,508 B2 | 9/2004 | Fraley et al. |
| 7,176,413 B2 * | 2/2007 | Zanella ................... F03G 7/065 |
| | | 219/202 |

(Continued)

FOREIGN PATENT DOCUMENTS

| DE | 10301489 B3 | 1/2004 |
| DE | 10303114 B3 | 8/2004 |

(Continued)

OTHER PUBLICATIONS

German Search Report dated Oct. 11, 2016 for German Application No. 102015226041.0, 6 pgs.

(Continued)

*Primary Examiner* — Todd M Melton
(74) *Attorney, Agent, or Firm* — Brooks Kushman P.C.

(57) ABSTRACT

The disclosure relates to a system for adapting at least one component of a vehicle. The vehicle component is operatively connected to an active material or formed from the active material. The active material is capable of changing at least one property in response to an activation signal. The activation signal is determined by at least one biometric variable of a vehicle occupant. Furthermore, the disclosure relates to a method for adapting a component of a vehicle.

18 Claims, 1 Drawing Sheet

(51) Int. Cl.
| | | |
|---|---|---|
| *B60K 37/04* | (2006.01) | |
| *A61B 5/01* | (2006.01) | |
| *A61B 5/021* | (2006.01) | |
| *A61B 5/0476* | (2006.01) | |
| *A61B 5/08* | (2006.01) | |
| *A61B 5/16* | (2006.01) | |
| *A61B 5/18* | (2006.01) | |
| *A61B 5/00* | (2006.01) | |
| *B60H 3/00* | (2006.01) | |
| *B60H 3/06* | (2006.01) | |
| *B60H 1/34* | (2006.01) | |
| *B60K 35/00* | (2006.01) | |
| *B60K 37/00* | (2006.01) | |
| *B60K 37/06* | (2006.01) | |

(52) U.S. Cl.
CPC .............. *B60H 3/06* (2013.01); *B60H 3/0658* (2013.01); *B60K 35/00* (2013.01); *B60K 37/00* (2013.01); *B60K 37/04* (2013.01); *B60K 37/06* (2013.01); *A61B 5/6893* (2013.01); *B60K 2350/2008* (2013.01); *B60K 2350/2043* (2013.01); *B60K 2350/355* (2013.01); *B60K 2350/357* (2013.01)

(56) References Cited

U.S. PATENT DOCUMENTS

| | | | |
|---|---|---|---|
| 7,284,786 B2 * | 10/2007 | Browne | B60J 7/04 296/107.01 |
| 7,370,894 B2 | 5/2008 | Browne et al. | |
| 7,517,279 B2 | 4/2009 | Kober et al. | |
| 7,997,632 B2 * | 8/2011 | Browne | B29C 33/308 293/128 |
| 8,377,347 B2 | 2/2013 | Sostmann et al. | |
| 8,485,581 B2 * | 7/2013 | McKnight | B60R 11/00 296/24.34 |
| 8,540,297 B2 * | 9/2013 | Browne | B60N 3/102 296/24.34 |
| 9,135,803 B1 | 9/2015 | Fields et al. | |
| 9,481,326 B2 * | 11/2016 | Chatterjee | H04W 4/046 |
| 2005/0157893 A1 | 7/2005 | Pelrine et al. | |
| 2007/0246285 A1 | 10/2007 | Browne et al. | |
| 2010/0140987 A1 | 6/2010 | Alexander et al. | |
| 2010/0282083 A1 | 11/2010 | Edwards | |
| 2015/0158244 A1 | 6/2015 | Tibbits et al. | |
| 2016/0226732 A1 * | 8/2016 | Kim | H04L 12/2807 |

FOREIGN PATENT DOCUMENTS

| | | |
|---|---|---|
| DE | 102005038680 A1 | 2/2006 |
| DE | 102007044978 A1 | 4/2009 |
| DE | 102008045015 A1 | 3/2010 |
| DE | 102013200192 A1 | 7/2013 |

OTHER PUBLICATIONS

Simon, "Bio-responsive architectural 3D prints can sense external environments", http://www.3ders.org/articles/20141211-bio-responsive-architectural-3d, Dec. 11, 2014, 13 pgs.

* cited by examiner

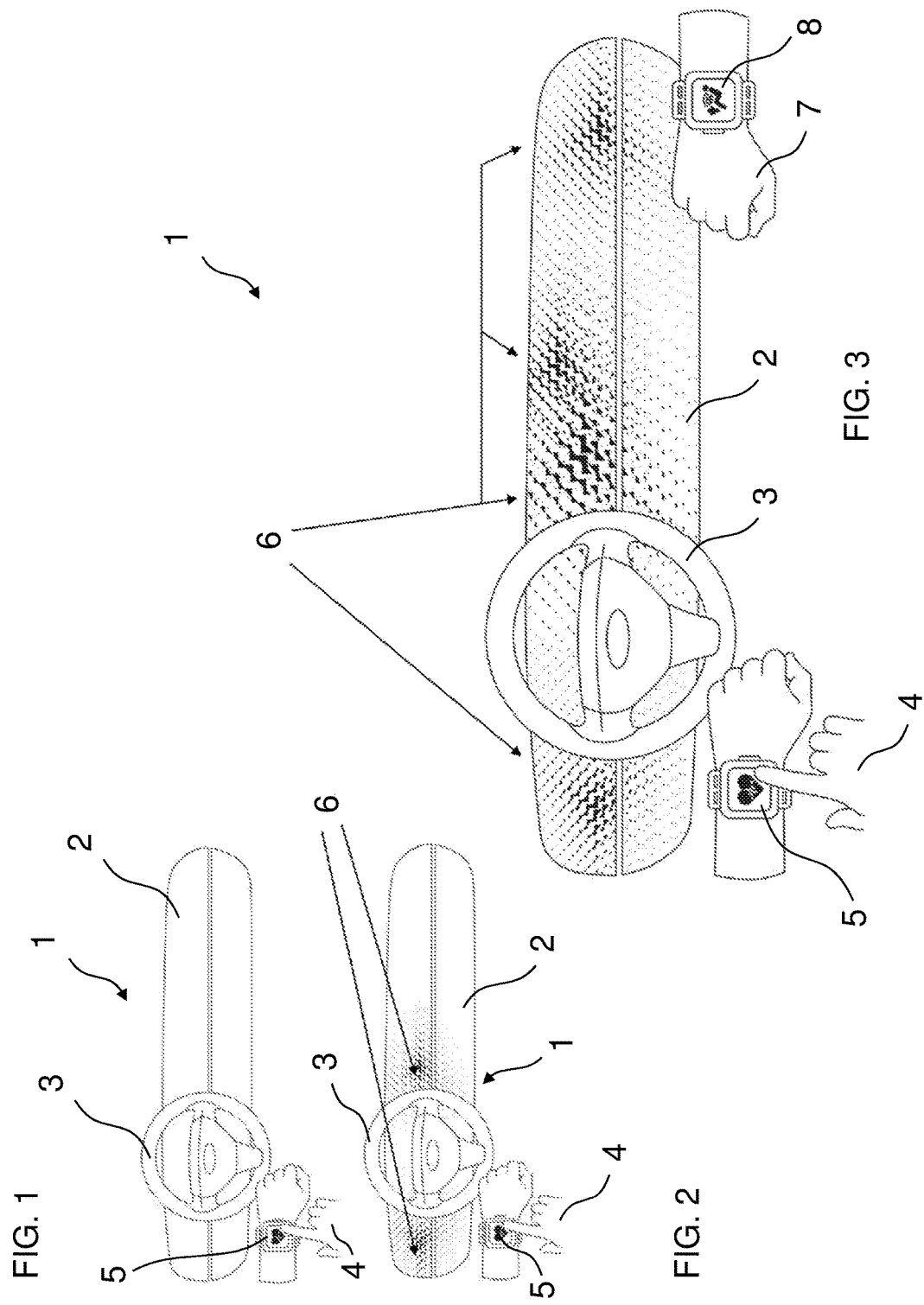

SYSTEM AND METHOD FOR ADAPTING A VEHICLE COMPONENT USING AN ACTIVE MATERIAL

CROSS-REFERENCE TO RELATED APPLICATIONS

This application claims foreign priority benefits under 35 U.S.C. § 119(a)-(d) to DE 10 2015 226 041.0 filed Dec. 18, 2015, which is hereby incorporated by reference in its entirety.

TECHNICAL FIELD

The present disclosure relates to a system and a method for adapting a vehicle component of a vehicle.

BACKGROUND

Changing properties of a component of a vehicle by using an active material is generally known. For example, U.S. Pat. No. 7,370,894 B2 shows a vehicle element that can be morphed as required, for example a body molding, which is operatively connected to or formed from an active material and which is in turn capable of changing a module property and/or a shape orientation in response to an activation signal. Thermal, electrical, magnetic, mechanical and pneumatic signals are listed as activation signals.

Furthermore, DE 10 2013 200 192 A1 discloses a system for the selective modification of the texture of an exposed surface by using a variably foldable structure, wherein the foldable structure interacts with an active material, which is capable of experiencing a reversible change of a property if it is subjected to an activation signal.

US 2005/0157893 A1 describes electro-active polymer converters, which convert electrical energy into mechanical energy and vice versa. This property is used to modify the texture of a surface selectively.

DE 10 2008 045 015 A1 also discloses a plastic skin as a surface coating for an object, for example a dashboard, having electroluminescent elements which represent luminous areas, texts, logos, warnings or information.

An architectural element produced by means of a 3D print, which is able to react to changes in external ambient conditions, such as moisture, for example, by means of a shape change, is described in the article "Bio-responsive architectural 3D prints can sense external environments", published online at the website of 3ders.org.

Against this background, the present disclosure is based on the object of providing a system and a method for adapting a vehicle component of a vehicle by using an active material.

SUMMARY

This object is achieved by a system and by a method. Further, particularly advantageous refinements of the disclosure are disclosed.

It should be pointed out that the features listed individually in the claims can be combined with one another in any desired technically practical manner and indicate further refinements of the disclosure. The description additionally characterizes and specifies the disclosure, in particular in conjunction with the figures.

According to the disclosure, a system for adapting at least one component of a vehicle, in particular a motor vehicle comprises an active material that is operatively connected to the vehicle component or forms the vehicle component. The active material is capable of changing at least one property, for example their shapes in response to an activation signal. According to the present disclosure, the activation signal is determined by at least one biometric variable of a vehicle occupant, for example a driver of the vehicle and/or one or more passengers. In other words, the activation signal is derived from at least one biometric variable of the vehicle occupant and in this way the active material is activated and deactivated.

Preferably, the vehicle component of the vehicle that is operatively connected to the active material or formed from the active material comprises in particular a dashboard, an inner door lining, a roof lining, a central console and/or a floor.

Biometric variables in the sense of the present disclosure can comprise physical properties of the vehicle occupant, such as in particular pulse, breathing rate, blood pressure, brain activity, body temperature or the like, and also variables derived therefrom, such as exhaustion or stress, for example, and the like.

As a result of the determination according to the disclosure of the activation signal, individualized activation and deactivation of the active material on the basis of the instantaneous given biometric variable, and consequently individualized adaptation of the vehicle component, is possible in a simple way.

According to an advantageous refinement of the disclosure, at least one electronic sensor that can be worn by the vehicle occupant is provided to detect the biometric variable. Particularly preferably, the electronic sensor can, for example, be a constituent part of a wristwatch worn by the vehicle occupant, such as a so-called smart watch, for example, which is able to detect one or more biometric variables of the wearer. Likewise, the electronic sensor can also be a constituent part of a brainwave headband which, for example, is able to detect the instantaneous brain activity of the wearer.

A further advantageous refinement of the disclosure provides that the at least one sensor can communicate by means of near-field communication, for example Bluetooth or infrared, with an electronic control device controlling the active material. In this way, the control device can activate and deactivate the active material on the basis of the biometric variable of the vehicle occupant detected by the sensor and thus adapt the vehicle component accordingly.

According to a still further advantageous refinement of the disclosure, the active material is an element produced by a so-called 4D print. The 4D print, known per se, is based technically on the 3D print, likewise known per se, and adds a further property to the elements produced by the 4D print: The 4D elements are capable of changing their shape and/or appearance over time and/or in response to an event, for example an activation signal. It is thus possible that the active material produced from a 4D print manages without additional electronic sensors to detect a biometric variable of a vehicle occupant and without any electronic control device for activating/deactivating the active material, since the active 4D material can already react automatically to certain biometric environmental variables, such as temperature, moisture and the like, for example. Accordingly, the vehicle component that is operatively connected to the active material or formed from the latter can adapt to the vehicle occupant individually without further action by the latter, without his having to activate a specific function by means of actuating a corresponding knob, for example.

A further advantageous refinement of the disclosure provides for the change in the property of the active material to comprise the changing of illumination integrated in the active material, such as for example by means of light-emitting diodes (LEDs) or organic light-emitting diodes (OLEDs). In this way, as a result of the activation/deactivation of the active material, for example, the biorhythm of the vehicle occupant, in particular with regard to current daytime or night-time, can be taken into account automatically and the vehicle interior can accordingly be adapted optimally hereto.

According to a further advantageous refinement of the disclosure, the change in the property of the active material comprises the opening or closing of a plurality of ventilation openings in the active material. Accordingly, it is possible to dispense with the provision of conventional statically presented ventilation openings in the vehicle interior, for example of an air conditioning system.

Still further advantageous refinements of the disclosure provide for the change in the property of the active material to comprise the liberation of a fragrance integrated in the active material and/or for the change in the property of the active material to comprise the activation of an air cleaning filter, in particular a biological air cleaning filter, integrated in the active material.

According to a further aspect of the present disclosure, a method is disclosed for adapting at least one vehicle component of a vehicle, in particular a motor vehicle, the vehicle component being operatively connected to an active material or formed from the latter. The active material is capable of changing at least one property in response to an activation signal. According to the disclosure, the active material is activated by at least one biometric variable of a vehicle occupant. With respect to further refinements of the method, its effects and advantages, reference is made to the above description, which is to be applied in an analogous way to the method according to the disclosure.

Further features and advantages of the disclosure can be gathered from the following description of an exemplary embodiment of the disclosure, which is not to be understood as restrictive and which is explained in more detail below with reference to the drawing. In this drawing, in schematic form:

BRIEF DESCRIPTION OF THE DRAWINGS

FIG. 1 shows a view of a system for adapting a vehicle component of a vehicle according to an exemplary embodiment of the disclosure in a first activation state, FIG. 2 shows the system from FIG. 1 in a second activation state, and FIG. 3 shows the system from FIG. 1 in a third activation state.

DETAILED DESCRIPTION

As required, detailed embodiments of the present disclosure are disclosed herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

In the different figures, parts that are equivalent with regard to their function are always provided with the same designations, so that said parts are generally also described only once.

FIG. 1 shows a view of a system 1 for adapting a vehicle component 2 of a vehicle (not illustrated in more detail) according to an exemplary embodiment of the disclosure in a first activation state. The vehicle component 2 illustrated in FIG. 1 is, by way of example, a dashboard 2 of the vehicle which, in the preferred embodiment, is a motor vehicle. The vehicle further comprises a steering wheel 3 for operating the motor vehicle by a vehicle occupant or a driver 4. In the exemplary embodiment illustrated in FIG. 1, the dashboard 2 is operatively connected to an active material or is formed entirely from the latter. The active material is capable of changing at least one property in response to an activation signal.

FIG. 1 further reveals an electronic sensor 5 that can be worn by the driver 4 in the form of a so-called smart watch, with the aid of which at least one biometric variable of the driver 4 can be detected. The smart watch 5 is communicatively connected via near-field communication, for example Bluetooth, to an electronic control device (not illustrated) in the vehicle, which ultimately generates the activation signal for the active material on the basis of the biometric variable detected. The activation state of the system 1 illustrated in FIG. 1 is that state in which initially all functions of the active material are deactivated.

With the aid of his smart watch 5, the driver 4 can trigger an activation signal for activating the active material, which signal is determined by at least one biometric variable of the driver 4 detected by the smart watch 5. This process is illustrated in FIG. 2, which shows a second activation state of the system 1 from FIG. 1. As a result of the activation of the active material by the activation signal, in the exemplary embodiment shown a plurality of ventilation openings 6 in the dashboard 2, which are indicated schematically in FIG. 2, have been opened. Since the driver 4 had triggered the activation signal, the ventilation openings have initially been opened in the dashboard 2 only in the area of the driver 4 (left-hand section of the dashboard 2). In the area of a passenger, not illustrated in FIG. 2 (right-hand section of the dashboard 2), the appearance of the dashboard 2 has not changed in comparison with the deactivated state illustrated in FIG. 1.

FIG. 3 illustrates the system 1 from FIG. 1 in a still further, second activation state. As can be seen in FIG. 3, an activation signal has now also been triggered by a further vehicle occupant 7 of the vehicle, who is a passenger 7, by means of a smart watch 8 worn by the passenger 7, which can detect at least one biometric variable of the passenger 7. As a result, by way of example, a plurality of ventilation openings 6 on the passenger side (right-hand section of the dashboard 2) has now also been opened by the active material in the dashboard 2.

The system and method according to the disclosure have been explained in more detail by using an exemplary embodiment illustrated in the figures. The system and the method are, however, not restricted to the embodiment described herein but also comprise further embodiments with the same effect.

In a preferred embodiment, the system and method according to the disclosure are used in a motor vehicle to adapt a vehicle component of the motor vehicle.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. An adaptation system of a vehicle comprising:
  a vehicle component operatively connected to, and formed from an active material, wherein the active material is configured to change, in at least one property including changing illumination integrated in the active material, in response to an activation signal; and
  at least one electronic sensor configured to generate the activation signal according to at least one biometric variable of a vehicle occupant.

2. The system as claimed in claim 1, wherein the least one electronic sensor is configured to be worn by the vehicle occupant such that contact between the at least one electronic sensor and the occupant detects the biometric variable to generate the activation signal.

3. The system as claimed in claim 1 further comprising: an electronic device configured to control the active material and communicate, via near field communication, with the at least one electronic sensor.

4. The system as claimed in claim 1, wherein the active material is an element produced by a 4D print.

5. The system as claimed in claim 1, wherein the change in the property of the active material comprises liberation of a fragrance integrated in the active material.

6. The system as claimed in claim 1, wherein the change in the property of the active material comprises activation of an air cleaning filter integrated in the active material.

7. The system as claimed in claim 1, wherein the change in the property of the active material comprises opening or closing of a plurality of ventilation openings in the active material.

8. The system as claimed in claim 1, wherein the vehicle component comprises a dashboard, an inner door lining, a roof lining, a central console, or a floor.

9. A method for adapting at least one component of a vehicle, comprising:
  forming the component from an active material, the active material changing in at least one property including liberating a fragrance integrated in the active material in response to an activation signal; and
  triggering the activation signal using at least one biometric variable, via an electronic sensor in near field communication with the active material.

10. The method as claimed in claim 9, wherein changing at least one property includes changing illumination integrated in the active material.

11. The method as claimed in claim 9, wherein changing at least one property includes activating an air cleaning filter integrated in the active material.

12. The method as claimed in claim 9, wherein changing at least one property includes opening or closing of a plurality of ventilation openings in the active material.

13. The method as claimed in claim 9, wherein the component is a center console of the vehicle.

14. A vehicle comprising:
  a dashboard formed from an active material configured to change a property responsive to an activation signal, and produced by a 4D print;
  a wearable electronic sensor configured to measure biometric variables and produce the activation signal based on the biometric variables indicative of exhaustion; and
  an electronic device configured to, in response to the biometric variables and receiving the activation signal from the electronic sensor, change the property of the dashboard.

15. The vehicle as claimed in claim 14, wherein the property is a plurality of ventilation openings in the dashboard.

16. The vehicle as claimed in claim 15, wherein the dashboard is further defined by first and second sections.

17. The vehicle as claimed in claim 16, wherein the first section of the dashboard is formed from the active material such that the electronic device is configured to, in response to the biometric variables and receiving the activation signal from the electronic sensor, change the property of the first section.

18. The vehicle as claimed in claim 16, wherein the second section of the dashboard is formed from the active material such that the electronic device is configured to, in response to the biometric variables and receiving the activation signal from the electronic sensor, change the property of the second section.

* * * * *